United States Patent
Abraham et al.

(10) Patent No.: US 6,838,562 B2
(45) Date of Patent: Jan. 4, 2005

(54) PROCESS FOR PREPARING A CREATINE HETEROCYCLIC ACID SALT AND METHOD OF USE

(76) Inventors: Sal Abraham, 1304 Electric St., Dunmore, PA (US) 18509; Shengli Jiang, Room 2105, Suite 4, No. 251 CaoXi Road, Shanghai N/A, 200233 (CN)

( * ) Notice: Subject to any disclaimer, the term of this patent is extended or adjusted under 35 U.S.C. 154(b) by 0 days.

(21) Appl. No.: 10/249,338

(22) Filed: Apr. 1, 2003

(65) Prior Publication Data

US 2004/0198823 A1 Oct. 7, 2004

(51) Int. Cl.$^7$ .................... C07D 239/22; C07D 239/56; A61P 21/06
(52) U.S. Cl. ........................................ 544/314; 514/274
(58) Field of Search .......................... 544/314; 514/269, 514/274

(56) References Cited

U.S. PATENT DOCUMENTS

| | | | |
|---|---|---|---|
| 3,944,550 A | | 3/1976 | Hasunuma et al. |
| 5,863,939 A | * | 1/1999 | Pischel et al. .............. 514/474 |
| 5,925,378 A | | 7/1999 | Carnazzo |
| 5,973,199 A | | 10/1999 | Negrisoli et al. |
| 6,114,379 A | | 9/2000 | Wheelwright et al. |
| 6,172,111 B1 | | 1/2001 | Pischel et al. |
| 6,177,576 B1 | * | 1/2001 | Arnold ....................... 549/372 |
| 6,211,407 B1 | | 4/2001 | Thomson |

OTHER PUBLICATIONS

Dena Mehlberg, "Creatine: Helpful or Harmful?", Sep. 26, 2000 [online] Milwaukee, WI: Medical College of Wisconsin, [retrieved on Apr. 7, 2004] Retrieved from the Internet <http://health.mcw.edu/article/969991656.html>.*
Ward, S. C. et al, "Systematic Study into the Salt Formation of Functionalised", [online] School of Chemistry, University of Southampton, [retrieved on Apr. 7, 2004] Retrieved from the Internet <http://www.nesc.ac.uk/events/ahm2003/AH-MCD/pdf/040.pdf>.*
Dawson, B. et al, J. Strength Cond. Res., 2002, 485–90, BioMedNet abstract only.*
Syrotuik DG, Game AB, Gillies EM, Bell GJ., Can J Appl Physiol. Dec. 2001;26(6):527–42. BioMedNet abstract only.*

* cited by examiner

*Primary Examiner*—Thomas C. McKenzie

(57) ABSTRACT

This invention relates to a process for the synthesis and method of use of an effective amount of a creatine heterocyclic acid salt for the regulation athletic function in humans.

9 Claims, No Drawings

PROCESS FOR PREPARING A CREATINE HETEROCYCLIC ACID SALT AND METHOD OF USE

Background of Invention

This invention relates to a process for the synthesis and method of use of an effective amount of a creatine heterocyclic acid salt for the regulation athletic function in humans. Creatine synthesis traditionally has utilized many forms ranging from free acid, salt, ester, amide, and hydrates. Creatine hydrates have been the preferred form, which may consist of a monohydrate salt, a dihydrate salt, a trihydrate salt, and a tetrahydrate salt. This is most likely due to the fact that the hydrate salts are thought to produce the most water soluble forms thereby possessing the most orally bioavailable forms. Although we purpose for the first time that the process for the synthesis and use of a creatine heterocyclic acid salt is novel, unobvious, and superior due to enhanced absorption, bioavailability and function.

Creatine is a nitrogenous organic acid that is found in muscle and nerve tissue. The body forms creatine from the amino acids arginine, glycine and methionine. Creatine is stored intramuscularly as creatine phosphate (phosphocreatine). Phosphocreatine donates its phosphate to adenosine diphosphate (ADP) to make adenosine triphosphate (ATP) and thus increases the rate of ATP regeneration, which promotes enhanced strength and endurance. Creatine is also thought to promote muscle mass via increasing the intracellular concentration of water, which is thought to activate protein synthesis and thus contribute to increases in strength, endurance and recovery.

Creatine has been patented for number of applications. For instance, U.S. Pat. No. 5,925,378 by Carnazzo demonstrates a method for enhancing delivery and uniformity of concentration of cellular creatine. U.S. Pat. No. 5,973,199 by Negrisoli et al. describes hydrosoluble organic salts of creatine. U.S. Pat. No. 6,172,111 by Pischel et al. demonstrates a method for producing creatine pyruvates. U.S. Pat. No. 6,114,379 by Wheelwright et al. further demonstrates a process for bioavailable chelates of creatine and essential metals. More recently U.S. Pat. No. 6,211,407 by Thomson describes a process for dicreatine citrate and tricreatine citrate and method of making same.

Creatine has been successfully utilized in a number of applications that either improve oral bioavailability or enhance function. While it is accepted that any improvement in creatine absorption should lead to enhanced creatine function, it is not equivalent to simultaneously improving creatine absorption while providing a synergistic compound that provides ergogenic benefit and acts as a functional salt carrier. The creatine heterocyclic acid salt may consist of a mono, di, or tri creatine orotate or derivative thereof. These novel and unobvious combinations provide a simultaneous synergistic action due to the use of mono, di and tricreatine cations, which are molecularly bonded to various forms of orotic acid, which in turn provide ergogenic functions while acting as efficient water soluble carriers or transporters. It should be understood that this invention is not construed as limited in scope by the details contained therein, as it is apparent to those skilled in the art that modification in materials and methods can be made without deviating from the scope of the invention.

Orotic acid (1,2,3,6-Tetrahydro-2,6-dioxo-4-pyrimidecarboxylic acid) is a heterocyclic organic acid that is a precursor of pyrimidine and therefore, has an influence on the metabolism of the nucleic acid. Orotic acid is also an intermediate in the manufacture of the pyrimidine bases such as uracil, cytosine, and thymine. Orotic acid at one time was classified as vitamin B 13, which was found to have growth-promoting and vitamin-like properties when added to the diets of laboratory animals as described by Rundles et al. Blood. 1958;13(2):99–115 and Moruzzi et al. Biochem Z. 1960;333:318–27. Orotic acid also provides an additional ergogenic benefit due to its role in the formation of uridine diphoshate (UDP) glucose, which is high energy form of glucose and a precursor to glycogen or the storage form of glucose. While orotic acid has been shown as a growth promoter and ergogenic aid it also has been shown to form stable water soluble electrostatic bonds with various minerals and vitamins such as magnesium orotate, calcium orotate, and vitamin E orotate as described in U.S. Pat. No. 3,944,550.

U.S. Pat. No. 5,973,199 by Negrisoli describes a method for producing stable hydrosoluble organic salts of creatine. Negrisoli states that the low water solubility of creatine dictates high oral doses for adequate creatine absorption. Negrisoli discloses a process for the synthesis of creatine citrate, maleate, fumarate, tartrate or malate anions. This combination produces higher water solubility from 3 to 15 times higher then that of creatine itself. This invention represents an improvement in standard creatine preparations due to the combination of creatine and the previously mentioned anions. However this combination only improves creatine absorption, which may lead to enhanced creatine function if adequate creatine storage occurs in the muscle cell. It does not provide a salt that simultaneously increases creatine absorption and provides a synergistic ergogenic effect to compliment the actions of creatine.

U.S. Pat. No. 6,172,111 by Pischel et al. demonstrates a method for producing creatine pyruvates. This combination is described to be physiologically safe, having a long shelf life, being highly soluble in water and having good bioavailability. Pischel discloses that creatine pyruvate may be of benefit for treating conditions of oxygen deficit (ischemia), overweight or obesity, preventing the formation of free radicals and scavenge free radicals or oxidizing species of oxygen, and enhancing long-term performance. This invention represents an improvement in standard creatine preparations due to the combination of creatine and pyruvate. However this combination only attempts to provide a long-term synergistic ergogenic benefit due to the ability of pyruvate to contribute to fat loss when administered in large doses. This combination can not provide acute or immediate synergistic ergogenic benefit, which is supported by research by Stone, et al. Int J Sport Nutr 1999 Jun;9(2):146–65, which demonstrates that pyruvate alone imparts no ergogenic benefit, which leads to the fact that the creatine portion is providing the only acute ergogenic benefit.

U.S. Pat. No. 6,114,379 by Wheelwright et al. demonstrates a process for bioavailable chelates of creatine and essential metals. Wheelwright states that it would be desirable to provide a creatine chelate for oral consumption comprised in such a way that the creatine ligand is protected by the metal from undergoing cyclization in the acidic environment of the stomach, thus making the creatine more readily available to the body in a useful form. This combination is described to enhance fatigue resistance and recovery time during high intensity, short-term exercise by providing a nutrient formulation, which is comprised of the anabolic nutrients phosphorus and creatine, which are precursors for the body's formation of phosphocreatine. It is also described to complement creatine and phosphorus with chelated magnesium as an activator of the enzymes that hydrolyze and transfer phosphate groups, e.g. the phosphatases and those concerned in the reactions involving adenosine triphosphate (ATP). This invention represents an improvement in standard creatine preparations due to the combination of creatine and mineral chelates. However this combination only improves creatine absorption, which may lead to enhanced creatine function if adequate creatine storage occurs in the muscle cell. It does not provide a salt that simultaneously increases creatine absorption and provides a synergistic ergogenic effect to compliment the actions of creatine. It is well known by those skilled in the art that minerals do not provide ergogenic benefit in healthy fed individuals but may provide benefit to those who are deficient in said minerals.

U.S. Pat. No. 6,211,407 by Thomson describes a process for dicreatine citrate and tricreatine citrate and method of making same. Thompson states that it would be desirable to provide another form of creatine that is stable, and that can prevent or impede the conversion of creatine to creatinine. It would further be desirable to provide a form of creatine salt that is other than a monocreatine citrate form of the salt. This invention represents an improvement in standard creatine preparations due to the combination of dicreatine/tricreatine and citrate. However this combination only improves creatine absorption, which may lead to enhanced creatine function if adequate creatine storage occurs in the muscle cell. It does not provide a salt that simultaneously increases creatine absorption and provides a synergistic ergogenic effect to compliment the actions of creatine.

SUMMARY OF INVENTION

The present invention consists of a process for the synthesis of a creatine heterocyclic acid salt and a method for the regulation of athletic function in humans. The method comprises administering to humans an effective amount of a composition consisting of an creatine heterocyclic acid salt such as but not limited to monocreatine orotate, dicreatine orotate, tricreatine orotate, and tricreatine thioorotate. These novel and unobvious combinations create a creatine heterocyclic acid salt in which both compounds are molecularly combined by an electrostatic bond.

The chemical synthesis of a creatine heterocyclic acid salt consists of a solution process and is capable of producing small or very large commercial amounts. The first step in the synthesis of a creatine heterocyclic acid salt begins with creatine monohydrate under room temperature, which is added to water appetent organic alcohol solvents, other water appetent organic solvents, or water. Then the heterocyclic acid salt is added to the mixture under room temperature. Finally filtration is utilized to remove the solvent and clean the residue with an organic alcohol or other water appetent organic solvents or water in order to obtain the finished product.

This creatine heterocyclic acid salt produces highly stable water soluble forms of creatine thereby substantially increasing oral absorption and bioavailability of the intact compound. Once the intact compound enters the blood stream it exerts a synergistic effect since both the creatine and heterocyclic acid derivative contribute to the promotion of lean tissue, endurance, strength by different mechanisms. In fact the electrostatically bound creatine heterocyclic acid salt possesses novel, unobvious and superior results to previous forms of creatine due to enhanced absorption, bioavailability and function and therefore may be utilized as a method for the regulation of athletic function in humans.

DETAILED DESCRIPTION

The chemical term creatine heterocyclic acid salt may refer but is not limited to tricreatine orotate with a molecular weight of 550.09. Possible alternative creatine cations include mono, di, and tricreatine while possible heterocyclic acids include orotic acid, thioorortic acid and dihydroorotic acid. This invention concerns a creatine heterocyclic acid salt in various ratios ranging from a 1:1 to 3:1 molar ratio and all previously mentioned alternatives. The previous examples of various ratios, cations, and heterocyclic acid salts are presented by way of illustration only. It should be understood that this invention is not construed as limited in scope by the details contained therein, as it is apparent to those skilled in the art that modifications in materials and methods can be made without deviating from the scope of the invention.

The solution synthesis of a creatine heterocyclic acid salt begins with creatine under room temperature, which is added to an organic alcohol or other water appetent organic solvents or water under agitation and stirring for 5 minutes to 90 minutes. The heterocyclic acid is slowly added to the mixture with continuous stirring for 1 hour to 8 hours under room temperature. Finally filtration is utilized to remove the solvent and dean the residue with water water appetent organic alcohol solvent, other water appented organic solvent, or water in order to obtain the creatine heterocyclic acid salt.

Balsom et al. Sports Med 1994 Oct;18(4):268–80 explains that ever since creatine was discovered in 1832 by Chevreul, it has intrigued researchers with its central role in skeletal muscle metabolism. In humans, over 95 percent of the total creatine content is located in skeletal muscle, which approximately a third is in its free form. Creatine and Creatine phosphate levels in skeletal muscle are subject to individual variations and are influenced by factors such as muscle fiber type, age and disease, but not apparently by training or gender. Daily turnover of creatine to creatinine for a 70 kilogram male has been estimated to be around 2 grams. A portion of this turnover can be replaced by the consumption of creatine containing foods such as meat and fish. The remainder is derived from endogenous synthesis of the amino acids arginine, glycine and methionine.

Harris et al. Clin Sci. 83, 367–374, 1992 found that low doses of 1 gram of creatine monohydrate produced only a modest rise in plasma creatine concentration whereas 5 gram resulted in a mean peak after 1 hour. Creatine is also found in red meat and one 5 gram dose is equal to 1.1 kilograms of uncooked steak. Supplementation with 5 grams of creatine monohydrate four to six times a day for 2 or more days resulted in a significant increase in the total creatine content of the quadriceps. They also found that the subjects with the lowest initial creatine content had the greatest increase in total creatine content after supplementation. The first two days of supplementation had the greatest uptake at 32 percent of the subjects receiving six 5 gram doses of creatine monohydrate. "Approximately 20 percent or more of the creatine taken up was measured as phosphocreatine (PCr)." Subjects performed one hour of hard exercise using one leg, which augmented the increase of creatine content in the exercised leg. This study shows that creatine monohydrate supplementation does increase total creatine and phosphocreatine of exercising muscles.

Greenhaff et al. Am J Physiol. 266, E725–730, 1994 has demonstrated the effects of creatine supplementation on skeletal muscle phosphocreatine resynthesis. In this study eight subjects had biopsies done after different recovery times from intense electrically evoked isometric contraction of one leg. After 10 days the same subjects had the other leg done but the subjects ingested 20 grams of creatine a day for 5 days preceding. "In five of the eight subjects creatine ingestion substantially increased muscle total creatine concentration and phosphocreatine resynthesis." This suggests a dietary increase in muscle total creatine content can increase phosphocreatine resynthesis. Also seen in 7 of 8 subjects was an increase in body weight after creatine ingestion. The data went on further to reveal that the subjects with the lowest prefeeding levels had the greatest increase in total creatine content and phosphocreatine resynthesis.

Greenhaff et al. Eur J Appl Physiol. 69, 268–270, 1994 determined the influence of creatine supplementation on performance during repeated bouts of isokinetic cycling in man. They looked at creatine supplementation during 3, 30 second bouts of maximal isokinetic cycling and on ammonia and lactate accumulation. The placebo group showed no effect on power output. Creatine ingestion of four 5 gram per day significantly increased peak power output and mean power output. But during the final bout of exercise the creatine group showed no effect of any measure. The ammonia level for the creatine group was lower even though they performed more work after the creatine ingestion. The placebo group showed no difference. There was also no difference on blood lactate levels of both placebo and creatine groups. "The lower accumulation of plasma ammonia under these conditions suggests this response is achieved by an effect on muscle ATP turnover."

Orotic acid is a heterocyclic organic acid that plays a pivotal role in biosynthetic pathway of pyrimidine metabolism. Pyrimidine metabolism produces pyrimidine nucleotide bases for the the storage of genetic information in the form of DNA and RNA. Pyrimidine biosynthesis begins with the condensation of aspartate and carbamoyl-phosphate in the cytoplasm to form N-carbamoyl-aspartate, which is then enzymatically converted to dihydroortic acid, which is further converted to orotic acid. Orotic acid is then linked with a phosphoribosylpyrophosphate (PRPP) for the formation of orotidine monophosphate (OMP), which is enzymatically decarboxylated to uridine monophosphate (UMP) for the phosphorylation of uridine diphosphate (UDP) and uridine triphosphate (UTP). UTP is then is then animated to form the end product cytidine triphosphate (CTP). The formation of pyrimidine nucleotides function as part of the building blocks for RNA and DNA in our cells yet another function of UMP, UDP, and UTP is glycogen synthesis.

One mechanism of orotic acid's ergogenic effect is due to its role in the formation uridine phosphates. Uridine phosphates also play a significant role in the formation of glycogen or the storage form of carbohydrates. Carbohydrates are the predominate fuel source for aerobic and anaerobic exercise depending upon the fed state of the individual. Adequate glycogen stores are crucial for optimal physical performance. Orotic acid is ultimately responsible for the formation of UDP-Glucose, which is an extremely high energy compound that donates glycosyl units to the glycogen chain and its the immediate precursor to glycogen synthesis. UTP also possesses ergogenic benefits due to its role in glycogen synthesis and its ability to donate phosphates for the formation of ATP and ADP. UTP hydrolysis is energetically equivalent to ATP hydrolysis.

Another mechanism of orotic acid's ergogenic effect is due to its vitamin like properties and growth promoting effects. Orotic acid was once referred to as vitamin B 13 due to its role with vitamin B12 and folate metabolism. Orotic acid has been demonstrated to spare vitamin B12 and folate in animals and thus compensate for deficiency. Adequate B vitamin stores are essential for carbohydrate metabolism, protein synthesis and red blood cell formation. Bal'magiia TA et al. Biull Eksp Biol Med 1975 Mar;79(3):18–21 describes orotic acid's ability to promote significant acceleration of growth and functional maturation of animals. These growth increases were attributed to increased oxygen consumption, frequency of respiration and cardiac contractions at rest.

The creatine heterocyclic acid salt promotes strength, endurance, recovery, lean tissue and decreases fat tissue. Thus the said compound can be given to humans either in conjunction with or without a high protein diet (1.25 to 1.8 grams protein/kilogram of body weight) and proper anaerobic training program in order to increase the variables associated with athletic function for the purpose of enhancing physical performance. Therefore this compound represents an improvement in standard dietary creatine supplementation, which may be utilized with humans for the regulation of athletic performance due to superior function.

After an extensive review of the scientific literature regarding the novel and unobvious synthesis of creatine heterocyclic acid salts and their superior absorption, bioavailability, and function, it then became the focus of this invention that creatine heterocyclic acid salts could be administrated perorally as an effective means of regulating athletic function in humans by promoting strength, endurance, recovery, lean body mass and decreasing fat mass. The oral daily doses can be between 1 to 40,000 mg. per day. The preferred daily dosing schedule should be one 5 gram dose post workout per day in order to achieve optimal absorption and adequate muscle cell concentrations.

In addition to peroral use, creatine heterocyclic acid salts can be effectively administered by several other routes including transdermal, sublingual, and intranasal. Creatine heterocyclic acid salts can also be administered in various dosage forms such as capsules, tablets, caplets, liquid, powder and functional food products.

The following examples illustrate a process for synthesis and method of use of a creatine heterocyclic acid salt. The following examples should not be considered as limitations of the present invention.

EXAMPLE 1

Synthesis of Creatine Orotate

Under room temperature 149 grams of creatine monohydrate is slowly added to 1.5 liters of ethanol under agitation and stirring for 30 minutes. Then 156 grams of orotic acid is slowly added to the mixture during continuous stirring for 4 hours under room temperature. Finally filtration is utilized to remove the solvent and clean the residue with ethanol. After drying 272 grams of creatine orotate is obtained.

EXAMPLE 2

Synthesis of Creatine Orotate with Water 2

Under room temperature 149 grams of creatine monohydrate is slowly added to 2 liters of water under agitation and stirring for 30 minutes. Then 156 grams of orotic acid is slowly added to the mixture and during continuous stirring for 4 hours under room temperature. Finally filtration is utilized to remove the water and clean the residue with water. After drying 270 grams of creatine orotate is obtained

EXAMPLE 3

Synthesis of DiCreatine Orotate

Under room temperature 298 grams of creatine monohydrate is slowly added to 2.5 liters of ethanol under agitation and stirring for 30 minutes. Then 156 grams of orotic acid is slowly added to the mixture during continuous stirring for 4 hours under room temperature. Finally filtration is utilized to remove the solvent and clean the residue with ethanol. After drying 410 grams of Dicreatine orotate is obtained.

EXAMPLE 4

Synthesis of TriCreatine Orotate

Under room temperature 447 grams of creatine monohydrate is slowly added to 3.5 liters of ethanol under agitation and stirring for 30 minutes. Then 156 grams of orotic acid is slowly added to the mixture during continuous stirring for 4 hours under room temperature. Finally filtration is utilized to remove the solvent and clean the residue with alcohol. After drying 555 grams of Tricreatine orotate is obtained.

EXAMPLE 5

TriCreatine Orotate Method of Use

In this example a 33 year old experienced weight trained male orally consumes 5 grams of tricreatine orotate post workout for 4 weeks with beverage. Glucose or any insulin potentiating compound may added for even greater results. In this instance the tricreatine orotate is incorporated into free powder mixture of flavoring agents and D-glucose, which is then combined with water. Once in the plasma tricreatine orotate then exerts a synergistic lean tissue promoting effect due to the anabolic actions of creatine and orotic acid. The creatine enhances phophocreatine resynthesis and attracts water to intercellular component of the muscle cell, which in turn activates protein synthesis while the orotic acid promotes uridine phosphates and glycogen synthesis. The previously mentioned physiological functions lead to increases in lean body mass, strength, endurance, recovery and loss of fat tissue. At the end of the 4 week period the individual reported a 6 pound weight gain, a 20 pound increase in his 1 repetition maximum bench press, and a 5 repetition increase in his initial 70 percent maximum bench press. These increases contribute to the regulation of athletic function and thus lead to enhanced physical performance.

The foregoing descriptions of the invention are for illustration only. Modifications not included in the description, which are obvious to those skilled in the art, are intended to be included in the scope of the following claims.

What is claimed is:

1. A process for the synthesis of creatine orotic acid, thioorotic acid, and dihydroorotic acid salt comprising the steps of:
   a) mixing creatine with water appetent organic alcohol solvents, other water appetent organic solvents, or water at a temperature of 1 to 100 degree Celsius,
   b) reacting the product of step a) with orotic acid, thioorotic acid, or dihydroorotic acid at a temperature of 1 to 100 degree Celsius;
   C) filtering to remove the solvent and washing the residue with water appetent organic alcohol solvents, other water appetent organic solvents, or water for the recovery of a mono, di, or tricreatine orotic acid, thioorotic acid, and dihydroorotic acid salt.

2. The process according to claim 1 step a), wherein the reaction is carried out at a temperature under 22 degree Celsius.

3. The process according to claim 1 step a), wherein said creatine is creatine monohydrate and said water appetent organic alcohol solvent is selected from the group consisting of methanol, ethanol, or propanol.

4. The process according to claim 1 step b), wherein the reaction is carried out at a temperature under 22 degree Celsius.

5. The process according to claim 1 step c), wherein the said water appetent organic alcohol solvent is selected from the group consisting of methanol, ethanol, and propanol.

6. A method for providing creatine to a human, comprising: receiving a creatine orotic acid, thioorotic acid, and dihydroorotic acid salt by the human, wherein the creatine orotic acid, thioorotic acid, and dihydroorotic acid salt is suitable for being modified by the human to form creatine.

7. The method as described in claim 6, wherein the creatine orotic acid, thioorotic acid, and dihydroorotic acid salt is suitable for peroral, transdermal, sublingual, and intranasal administration.

8. The method as described in claim 6, wherein the creatine orotic acid, thioorotic acid, and dihydroorotic acid salt is suitable in a daily dose of 1 to 40,000 mg/day.

9. The method as described in claim 6, wherein the creatine orotic acid, thioorotic acid, and dihydroorotic acid salt is received by the human, the creatine orotic acid, thioorotic acid, and dihydroorotic acid salt is modified by the human into creatine and orotic acid, thioorotic acid, and dihydroorotic acid.

* * * * *